(12) United States Patent
Sabherwal et al.

(10) Patent No.: US 12,214,074 B2
(45) Date of Patent: Feb. 4, 2025

(54) APPLICATOR HEAD WITH DOSING AID

(71) Applicant: HALEON CH SARL, Prangins (CH)

(72) Inventors: Amit Sabherwal, Gurgaon Horizon (IN); Sylvain Patrice Dominique Fradin, Nyon (CH)

(73) Assignee: HALEON CH SARL, Prangins (CH)

( * ) Notice: Subject to any disclaimer, the term of this patent is extended or adjusted under 35 U.S.C. 154(b) by 786 days.

(21) Appl. No.: 17/184,850

(22) Filed: Feb. 25, 2021

(65) Prior Publication Data

US 2022/0265550 A1    Aug. 25, 2022

(51) Int. Cl.
*A61J 1/00*    (2023.01)
*A61K 9/06*    (2006.01)
(Continued)

(52) U.S. Cl.
CPC .............. *A61K 9/06* (2013.01); *B29C 45/18* (2013.01); *B65D 35/36* (2013.01); *B65D 35/40* (2013.01);
(Continued)

(58) Field of Classification Search
CPC .... A45D 2200/10; A45D 34/04; A45D 34/00; A45D 34/041; A61J 1/00; A61J 3/00; A61K 9/06; A61M 35/003; B29C 45/16; B29C 45/18; B65D 35/36; B65D 35/40; B65D 83/00; B65D 83/04
See application file for complete search history.

(56) References Cited

U.S. PATENT DOCUMENTS 2,961,679 A * 11/1960 Claypool ............... A45D 40/26
                                                    401/266
D827,433 S * 9/2018 Bickford ..................... D24/119
(Continued)

FOREIGN PATENT DOCUMENTS

DE       102018204939 A1 * 10/2019  ............. A45D 34/04
EP       3 909 464 A1       11/2021
WO     WO-2021228607 A1 * 11/2021  ............. A45D 34/04

OTHER PUBLICATIONS

International Search Report of International Application No. PCT/EP2022/054463 mailed May 24, 2022.
(Continued)

*Primary Examiner* — Leslie A Lopez
*Assistant Examiner* — Jihad Dakkak
(74) *Attorney, Agent, or Firm* — E. Eric Mills; Nicholas P. Stadnyk; Maynard Nexsen PC (57) ABSTRACT

There is provided an applicator head (10) for administration of a topical formulation, comprising a dosing aid for application of a predefined dose of the topical formulation. The applicator head (10) comprises an applicator surface (20) adapted to apply the topical formulation to a user's skin. The applicator surface (20) comprises an outlet opening (40). The dosing aid comprises a dose marking, or dose markings (60, 60', 60", 62', 62") on the applicator surface (20), wherein the dose marking (60, 60', 60", 62', 62") has a circular outline and a diameter D, and wherein the outlet opening (40) is disposed in the center of the circular outline, and wherein the dose marking (60, 60', 60", 62', 62") circumscribes an inner dosing compartment (64) that serves to measure the predefined dose of the topical formulation.

17 Claims, 5 Drawing Sheets

(51) Int. Cl.
  *B29C 45/18* (2006.01)
  *B65D 35/36* (2006.01)
  *B65D 35/40* (2006.01)
  *B65D 83/00* (2006.01)
  *A61J 3/00* (2006.01)
  *B65D 83/04* (2006.01)

(52) U.S. Cl.
  CPC .. *A61J 1/00* (2013.01); *A61J 3/00* (2013.01); *B65D 83/00* (2013.01); *B65D 83/04* (2013.01)

(56) References Cited

U.S. PATENT DOCUMENTS

| | | | |
|---|---|---|---|
| 11,559,126 B1* | 1/2023 | Samangooie | A45D 34/04 |
| 2002/0048481 A1* | 4/2002 | Gueret | A45D 33/00 |
| | | | 401/126 |
| 2014/0221943 A1* | 8/2014 | Carrara | A61K 31/568 |
| | | | 604/310 |
| 2016/0095414 A1 | 4/2016 | Debnath et al. | |
| 2018/0207413 A1* | 7/2018 | Skakoon | A61J 1/2065 |
| 2021/0178135 A1* | 6/2021 | Brinkman | A61Q 15/00 |

OTHER PUBLICATIONS

Written Opinion of the International Searching Authority of International Application No. PCT/EP2022/054463 mailed May 24, 2022.

* cited by examiner

APPLICATOR HEAD WITH DOSING AID

FIELD OF THE INVENTION

This application is directed to improved applicator heads for application of topical formulations such as creams or gels.

BACKGROUND TO THE INVENTION

Specialized packaging for topical formulations such as creams, gels, ointments or the like can be equipped with applicator heads. Applicator heads comprise an outlet opening for expulsion of product from the packaging, and an applica surface for rubbing the expelled product into the skin. An example of such a packaging is disclosed in WO2014/170841. Applicator surfaces can additionally comprise surface undulations such as massage bumps. Surface undulations provide a massage effect when an applicator head is used to rub product into the skin.

These types of packaging with applicator heads however do not comprise any means for dosing of a product. With packaging of the art, the only way to achieve adequate dosing of a topical formulation is by applying a line of product of a prescribed length onto the skin. Users, when applying a line of product, have to estimate a length of this line of product. Instructions for use usually prescribe a length for a predefined dose. Estimation is however not a precise way of dosing. Doses applied can vary significantly. Especially in the field of topical medicines, this is not acceptable in view of patient safety. Therefore, in other cases, users measure a length of a line of product with help of a dosing card. A dosing card usually is a plastic card comprising a printed line of a predefined length. The printed line is used as a reference. For example, a dosing card can comprise a printed line of a length of 6 cm, which corresponds to a predefined dose. A user has to position the dosing card on his or her skin, and then apply a line of product, having the same length as the reference line on the dosing card, onto the skin. Alternatively, a user has to dose a line of product having the same length as the reference line onto the dosing card, and then apply the product from the dosing card to the desired skin area. Dosing with a dosing card may be more accurate than dosing based on estimation. However, dosing with a dosing card is more difficult, unhygienic, and inconvenient. This dosing and application procedure can therefore be cumbersome for users and be especially difficult for patients who use a topical formulation for the treatment of pain, such as arthritis, as they have to handle both the container of the product and the dosing card simultaneously to dispense an accurate dose. It can furthermore often be messy when the package, the dosing card, or the hands of the user are spilled with product. The dosing card then has to be cleaned and dried for storage and further use. The dosing card can also be lost by the user. Additionally, users sometimes do not understand how to use the dosing card.

Both, dosing with and without a dosing card, have another significant drawback. With both dosing methods, users cannot benefit from using an applicator surface to rub the product directly onto the desired area.

There is thus a need for a dosing method and dosing aid that can be used in combination with applicator heads for packaging of topical compositions. This is especially crucial for the packaging of topical medicines. The dosing aid should allow precise dosing. It should allow easy handling and intuitive dosing. The dosing procedure should be clean and not messy. It should require a minimal number of parts.

SUMMARY

This disclosure provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation.

In one embodiment, diameter D is selected such that, when the topical formulation is ejected from the outlet opening, the amount of topical formulation that spreads from the outlet opening and over the inner dosing compartment until it reaches the dose marking, corresponds to the predefined dose.

In one embodiment, the dose marking is a visual dose marking.

In one embodiment, the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface.

In one embodiment, the dose marking has a color that is different from the color of a rest of the applicator surface.

In one embodiment, the dose marking flushes with the applicator surface.

In one embodiment, the dosing aid is adapted for dosing of two predefined doses of topical formulation.

In one embodiment, there is more than one dose marking on the applicator surface, and the dose markings are arranged on the applicator surface concentric around the outlet opening.

In one embodiment, there are a first and a second dose marking on the applicator surface, wherein the first dose marking is arranged between the outlet opening and the second dose marking, and wherein the first and second dose marking between them circumscribe a ring dosing compartment, and wherein the ring dosing compartment has a ring width W that is the distance between the first and the second dose marking.

In one embodiment, the ring width W is selected such that when the topical formulation is ejected from the outlet opening, the amount of topical formulation that spreads from the outlet opening and over the inner dosing compartment and further over the ring dosing compartment until it reaches the second dose marking, corresponds to a second predefined dose.

In one embodiment, the applicator surface is manufactured by bi-injection moulding.

In one embodiment, the diameter D of the first dose marking is about 19 mm to about 21 mm.

In one embodiment, the diameter D of the second dose marking is about 25 mm to about 27 mm and the ring width W is about 0.8 mm to about 3 mm.

There is also provided an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises multiple outlet openings, and wherein the dosing aid comprises a dose marking on the applicator surface, wherein the dose marking has a circular outline and a diameter D, and wherein the outlet openings are disposed on the applicator surface point symmetrically to a center of the circular outline, and wherein the dose marking circumscribes an inner dosing compartment that serves to measure the predefined dose of the topical formulation.

There is also provided a packaging for a topical formulation comprising an applicator head as disclosed herein.

There is furthermore provided a product comprising a packaging as disclosed herein. There is furthermore provided a product as described herein, wherein the topical formulation has a viscosity in the range of 1 Pa·s to 4 Pa·s.

There is also provided a method of dosing the topical formulation according to comprising the steps of: urging the topical formulation from the packaging and out of the outlet opening on the applicator surface, letting the topical formulation spread over the applicator surface until it covers the inner dosing compartment, and stopping urging of the topical formulation as soon as the topical formulation covers the inner dosing compartment. This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, and wherein the dose marking is a visual dose marking.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, wherein the dose marking is a visual dose marking, and wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, and wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the dose marking is a visual dose marking, and wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface, wherein the dose marking has a color that is different from the color of a rest of the applicator surface.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, wherein the dose marking is a visual dose marking, wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface, and wherein the dose marking has a color that is different from the color of a rest of the applicator surface.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, wherein the dose marking is a visual dose marking, wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface, and wherein the dose marking has a color that is different from the color of a rest of the applicator surface, and wherein the dose marking flushes with the applicator surface.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, wherein the dose marking is a visual dose marking, wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface, wherein the dose marking has a color that is different from the color of a rest of the applicator surface, and wherein the dosing aid is adapted for dosing of two predefined doses of topical formulation.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, wherein the dose marking is a visual dose marking, wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface, wherein the dose marking has a color that is different from the color of a rest of the applicator surface, wherein the dosing aid is adapted for dosing of two predefined doses of topical formulation, wherein there is more than one dose marking on the applicator surface, and wherein the dose markings are arranged on the applicator surface concentrically around the outlet opening.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, wherein the dose marking is a visual dose marking, wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface, wherein the dose marking has a color that is different from the color of a rest of the applicator surface, wherein the dosing aid is adapted for dosing of two predefined doses of topical formulation, wherein there is more than one dose marking on the applicator surface, wherein the dose markings are arranged on the applicator surface concentrically around the outlet opening, and wherein there are a first and a second dose marking on the applicator surface, wherein the first dose marking is arranged between the outlet opening and the second dose marking, and wherein the first and second dose marking between them circumscribe a ring dosing compartment, and wherein the ring dosing compartment has a ring width W that is the distance between the first and the second dose marking.

This disclosure also provides an applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking has a circular outline and a diameter D, and wherein the outlet opening is disposed in the center of the circular outline, and wherein the dose marking circumscribes an inner dosing compartment that serves to measure the predefined dose of the topical formulation, wherein the diameter D is selected such that, when the topical formulation is ejected from the outlet opening, the amount of topical formulation that spreads from the outlet opening and over the inner dosing compartment until it reaches the dose marking, corresponds to the predefined dose, wherein the dose marking is a visual dose marking, wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface, wherein the dose marking has a color that is different from the color of a rest of the applicator surface, wherein the dosing aid is adapted for dosing of two predefined doses of topical formulation, and wherein there is more than one dose marking on the applicator surface, wherein the dose markings are arranged on the applicator surface concentrically around the outlet opening, and wherein there are a first and a second dose marking on the applicator surface, wherein the first dose marking is arranged between the outlet opening and the second dose marking, and wherein the first and second dose marking between them circumscribe a ring dosing compartment, wherein the ring dosing compartment has a ring width W that is the distance between the first and the second dose marking, and wherein the ring width W is selected such that when the topical formulation is ejected from the outlet opening, the amount of topical formulation that spreads from the outlet opening and over the inner dosing compartment and further over the ring dosing compartment, until it reaches the second dose marking, corresponds to a second predefined dose.

DETAILED DESCRIPTION

FIGS. 1-8 illustrate an applicator head (10) according to embodiments of the present invention. The present invention is directed to an application head (10) comprising an applicator surface (20) having a dosing aid. The dosing aid is suitable for measuring a predefined dose of a topical formulation. The dosing aid comprises a dose marking (60), and in some embodiments multiple dose markings (60', 62', 60", 62"). The dose markings (60, 60', 60", 62', 62") are formed on the applicator surface (20).

Applicator Head

The present disclosure provides for an applicator head (10) comprising an applicator surface (20). The applicator head (10) can be mounted onto a container or connected to a container, for example a tube or a can. Alternatively, the applicator head (10) can be formed in one piece with a container.

The applicator surface (20) is preferably substantially flat. The applicator surface (20) may be formed in one piece with the applicator head (10) or may be a separate piece, connectable to an applicator head body (11). The applicator surface (20) comprises a bottom side facing the applicator head body (11). Opposite the bottom side, the applicator surface (20) has an upper side, facing outwards, or facing a user.

The applicator surface (20) can be laterally limited by an end wall (30). The end wall (30) can extend from the bottom side of the applicator surface (20). Preferably, the applicator surface (20) is substantially circular. A circular applicator surface (20) provides the best results in terms of product distribution and sensation upon application of topical formulation to skin. Circular form of the applicator surface (20) is especially preferred for applicator heads used for massaging, as the circular form does not have edges which could pinch or scratch when pressed onto skin with massage pressure. The applicator surface (20) is adapted for application of a topical formulation on a user's skin. A user can thus use the applicator head (10) instead of his or her hands to apply a topical formulation. Thereby, the user's hands are kept clean. For example, the applicator surface (20) can be adapted for rubbing or massaging of a topical skin cream into a user's skin. This means in particular that the applicator surface (20) has a smooth upper surface without sharp edges or similar surface structures which could cause an unpleasant sensation. Such a smooth surface also ensures that the topical formulation, skin scales or the like cannot accumulate on the applicator surface (20). A smooth surface also provides skin friendly haptics. A smooth upper surface is furthermore preferred as it enables topical formulation to spread uniformly across the applicator surface (20).

The applicator surface (20) can be made from a plastic material. Plastic material provides a strength suitable to use the applicator surface (20) for massaging. Alternatively, the applicator surface (20) may be from a sponge or fabric material. The sponge or fabric material can partially absorb the topical formulation and release the formulation when the applicator surface (20) is pressed onto the skin. Applicator surfaces (20) made from sponge or fabric material provide a soft and gentle application experience and reduce the risk of dripping of topical formulation.

The applicator surface (20) can be flat or can comprise surface undulations (80). Surface undulations (80) are protrusions of the applicator surface (20) that protrude from the upper side. An example of surface undulations (80) are massage bumps. Surface undulations (80) provide a massaging effect when the applicator head (20) is used to apply a topical formulation. Due to surface undulations (80), the applicator surface (20) can have a wavy or rippled surface profile. In a preferred embodiment, the applicator surface (20) comprises surface undulations (80) which are rounded. Rounded surface undulations (80) are preferred to avoid ridges or edges on the applicator surface (20). Surface undulations (80) preferably protrude from the applicator surface (20) from about 0.5 mm to about 1.0 mm. Surface undulations (80) of this height of protrusion provide a massaging effect whilst not hindering uniform spread of topical formulation across the applicator surface (20).

Within the applicator surface (20) there is formed an outlet opening (40). The outlet opening (40) is a hole in the applicator surface (20). Preferably, the outlet opening (40) is circular. Circular outlet openings (40) form uniformly thick, round lines of topical formulation, which is beneficial for uniformity of dosing. There may be one single outlet opening (40) or there may be multiple outlet openings arranged on the applicator surface (20). In embodiments with multiple outlet openings (40), the outlet openings (40) preferably are disposed on the applicator surface (20) point symmetrical. For example, there may be formed from about five to about eleven outlet openings (40) formed on the applicator surface (20), arranged in a circle of outlet openings.

In embodiments with one outlet opening (40), the outlet opening (40) preferably has a diameter of about 2.5 mm to about 5 mm. Diameters of this range are suitable for easy expulsion of most topical formulations with their typical viscosity and flow characteristics. Diameters of this range are at the same time suitable for precise expulsion, especially of small doses of topical formulation, such as 2 grams. The outlet opening (40) can communicate with a flow conduit which is formed inside the applicator head. When the applicator head (10) is connected to a container comprising topical formulation, the flow conduit connects an inside of the container to the outside. Topical formulation can thus be urged out of the container, through the flow conduit and out of the outlet opening (40). Upon expulsion, topical formulation can flow through the applicator head (10) in a flow direction A-A'. In some embodiments, the applicator surface (20) is arranged perpendicular towards the flow direction A-A'. In other embodiments, the applicator surface (20) is arranged in a uniform acute angle towards the flow direction A-A'. These perpendicular and acute angle arrangements of the applicator surface (20) are preferred because they result in laminar flow of topical formulation and reliable uniform spread of topical formulation on the applicator surface (20).

The applicator surface (20) can optionally comprise an outlet rim (50). The outlet rim (50) borders the outlet opening (40). The outlet rim (50) is an annular protrusion protruding from the applicator surface (20). The outlet rim (50) has the outlet opening (40) in its center. The outlet rim (50) can protrude from the applicator surface (20) about 1 mm to about 2 mm above a level at which it merges with the applicator surface (20). The outlet rim (50) can aid uniform, circular spread of topical formulation across the applicator surface (20).

In some embodiments, the applicator surface (20) can have a curvature. Preferably, the applicator surface (20) has a curvature, the curvature being spheroidal convex from the outlet opening (40) to the end wall (30). The highest point of the curvature can be close to the outlet opening (40) and the lowest point of the curvature can be near the end wall (30). In one embodiment, the height difference between the highest point of the curvature and the lowest point of the curvature is about 0.75 mm to about 2 mm. This convex curvature in the applicator surface (20) facilitates application and massaging. It also facilitates spread of product on the applicator surface (20), by gravity. This is especially preferred for topical formulations with a viscosity of 1.5 Pa·s or higher.

In embodiments with circular applicator surfaces (20), the outlet opening (40) preferably is formed centrally on the applicator surface (20). This is preferred because thereby, a user can intuitively spot the outlet opening (40) on the applicator surface (20). It is also preferred because thereby, outlet opening (40), applicator surface (20) and a dosing aid comprising dose markings (60, 60', 60", 62', 62"), can be arranged concentrically to the outlet opening (40). Concentric arrangement facilitates understanding of the dosing aid.

The applicator head (10) comprises a dosing aid. The dosing aid is suitable for measuring of a predefined dose of a topical formulation. The dosing aid comprises a dose marking (60), and in some embodiments multiple dose markings (60', 62', 60", 62"). The dose markings (60, 60', 60", 62', 62") are formed on the applicator surface (20). The dose markings (60, 60', 60", 62', 62") have a circular outline and a diameter D. The diameter D is adapted to a predefined dose of topical formulation, to be measured with the dosing aid. Methods of adjusting diameter D to predefined doses of topical formulations are described in a separate section below. The dose markings (60, 60', 60", 62', 62") are positioned on the applicator surface (20) with the outlet opening (40) in their center. In other words, the outlet opening (40) is disposed in the center of the circular outline of the dose markings (60, 60', 60", 62', 62"). In embodiments with two or more dose markings, the dose markings (60, 60', 60", 62', 62") have different diameters D and are arranged concentrically around the outlet opening (40). In embodiments with multiple outlet openings (40), the outlet openings (40) are disposed on the applicator surface (20) point symmetrical to a center of the circular outline of the dose marking(s).

Two dose markings circumscribe between them a ring dosing compartment (66). Ring dosing compartments (66) have ring widths W. Methods of adjusting diameters D and ring widths W to first, second and further predefined doses of topical formulation are described in a separate section below.

The dose markings (60, 60', 60", 62', 62") can be realized on the applicator surface (20) in numerous ways. For example, the dose markings (60, 60', 60", 62', 62") can be realized by embossing, application of color, imprinting, printing, molding-in, in-mold labelling, surface treatment, laser etching, laser engraving or stickering. The dose markings (60, 60', 60", 62', 62") can for example be haptic dose markings, visual dose markings, or a combination thereof. Preferably, the dose markings are visual dose markings. That means, the dose markings can be perceived visually by a user on the applicator surface (20). Visual dose markings are preferred as they are easily noticed and understood by most users. More preferably, the dose markings (60, 60', 60", 62', 62") are only visual dose markings. In other words, the dose markings (60, 60', 60", 62', 62") do not protrude from or incise in the applicator surface (20), i.e., the dose markings do not alter a surface profile of the applicator surface (20). This is preferred as thereby the preferred smooth surface of the applicator surface (20) can be maintained, and massaging and ease of application with the applicator head (10) is not hampered by the dose markings (60, 60', 60", 62', 62").

Furthermore, provided the topical formulation has a suitable viscosity, dose markings (60, 60', 60", 62', 62") which are only visual dose markings lead to more precise dosing results, whereas a dose marking protruding from the applicator surface could for example lead to an accumulation of product in the region of the applicator head (20') inwards of the respective dose marking (60, 60', 60", 62', 62"), for example an inner dosing compartment (64), and thus to a quantity of topical formulation not being well defined.

In embodiments with visual dose markings, it is preferred that the dosing compartment or dosing compartments, the dose marking or dose markings (60, 60', 60", 62', 62"), or both, differ from a rest of the applicator surface (20) in color. Preferably, colors are chosen that differ strongly, such that a demarcation between different colors is readily apparent. In some embodiments, a rest of the applicator surface (20) has a color similar to a color of the topical formulation to be dosed with the applicator head (10), and the dose marking(s) (60, 60', 60", 62', 62") have a different color. This facilitates dosing with the applicator head, as it can instantaneously be seen when the topical formulation covers a dosing compartment or reaches a dose marking. Preferably, to create a high contrast, the colors should be as apart as possible on a color wheel, such as light and dark shades. Also preferred are primary colors, or colors close to primary colors. In one embodiment, the dose marking(s) (60, 60', 60", 62', 62") have an orange color and a rest of the applicator surface (20) has a white color. Orange and white color are especially preferred, as they have a high contrast, and as most topical formulations are opaque to white. This facilitates dosing with the applicator head (10).

The dose markings (60, 60', 60", 62', 62") can be standalone features, such as lines, broken lines or rings. Alternatively, a demarcation between areas on the applicator surface that have different characteristics can serve as the dose marking or dose markings. For example, a line of demarcation between two differently colored compartments of the applicator surface can constitute a dose marking.

In embodiments comprising one dose marking (60), the dose marking (60) circumscribes an inner dosing compartment (64) on the applicator surface (20). A remaining area of the applicator surface (20) is an outer compartment (68). Outer compartment (68) is not used for dosing. The inner dosing compartment (64) serves to measure one predefined dose of topical formulation. Methods of dosing with the applicator head (10) comprising one dose marking (60) are described in a separate section below.

In embodiments comprising more than one dose marking (60', 60", 62', 62"), a first or innermost dose marking (60', 60"), i.e., the dose marking with the smallest diameter D, circumscribes the inner dosing compartment (64). The inner dosing compartment (64) serves to measure a first predefined dose of topical formulation. A second dose marking (62', 62") is a dose marking with the second smallest diameter D. First and second dose marking (60', 60", 62', 62") between them circumscribe a first ring dosing compartment (66). A first ring dosing compartment (66) is an area on the applicator surface (20) that is delimited inwardly by a first dose marking (60', 60") and delimited outwardly by a second dose marking (62'. 62"). The ring dosing compartment (66) has a ring width W. The ring dosing compartment (66), together with the inner dosing compartment (64), serves to measure a second predefined dose of topical formulation. A remaining area of the applicator surface, i.e., outwardly from the second dose marking (62', 62"), is an outer compartment (68).

The applicator head (10) can comprise a third dose marking and further dose markings, all dose markings being arranged concentrically and each dose marking having a wider diameter D than the previous dose marking. Multiple dose markings circumscribe multiple ring dosing compartments, analogous to what was described above for two dose markings. Methods of dosing with the applicator head comprising two or more dose markings are described in a separate section below.

The dose markings (60, 60', 60", 62', 62") divide the applicator surface (20) into compartments. Embodiments comprising one dose marking (60) comprise one dosing compartment (64), suitable to measure one predefined dose of topical formulation. Embodiments comprising two dose markings (60', 60", 62', 62") comprise two dosing compartments (64, 66), suitable to measure two predefined doses of topical formulation, etc. An area outwardly from an outermost dose marking is an outer compartment (68), which is not used for dosing. When topical formulation is urged out of the outlet opening (40), the topical formulation spreads evenly in a circular formation filling the dosing compartment(s) (64, 66).

In some embodiments, the inner dosing compartment (64) has a different color than the outer compartment (68). In some embodiments, the applicator surface (20) is molded from multiple materials, and borders between the materials constitute the dose marking (60) or dose markings (60', 60", 62', 62"). The materials can be the same or distinct plastic materials, such as HDPE, LDPE, Poly Propylene, Poly Carbonate or Silicon. Preferred is HDPE. Preferably, the materials differ in color.

In another embodiment, the dose marking (60) or dose markings (60', 60", 62', 62") are laser etched circular lines on the applicator surface (20). The lines can be continuous or can be broken lines.

In one embodiment, the applicator surface (20) comprises a ring (65). The ring (65) can be molded into the applicator surface (20) by bi-injection molding, which is a technique known in the art. For example, a body of the applicator surface (20) can be molded from a first material in a first molding step. In this first molding step, an annular recess (67) is foreseen in the body. The recess may be about 0.75 mm to about 1.5 mm deep from the applicator surface (20). Preferred is a recess of about 0.9 mm deep from the applicator surface (20). In a second molding step, this recess (67) can be filled with a second material of the ring (65).

Figure 2:
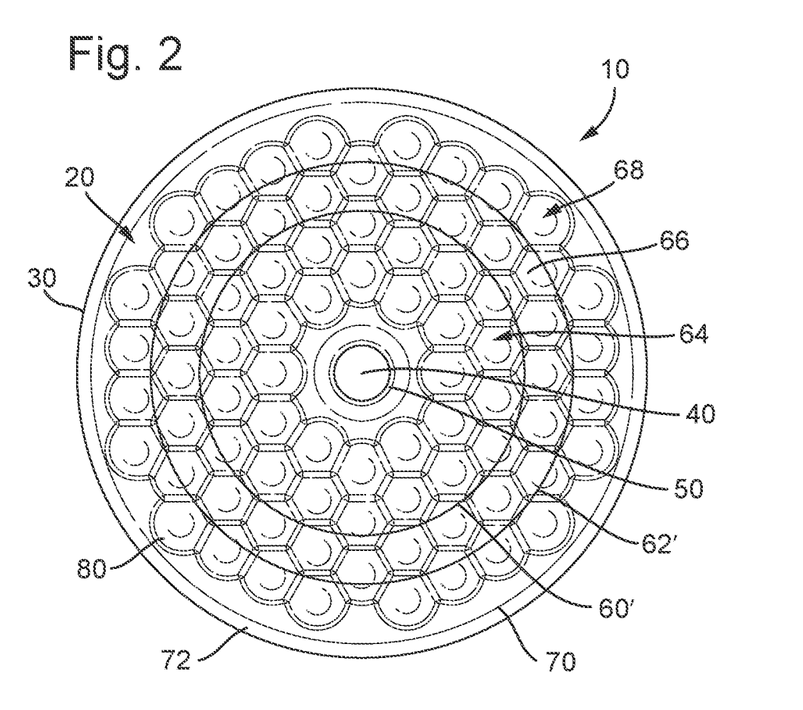
FIG. 2 shows a top view of a second embodiment of an applicator head with dosing aid.
Figure 3:
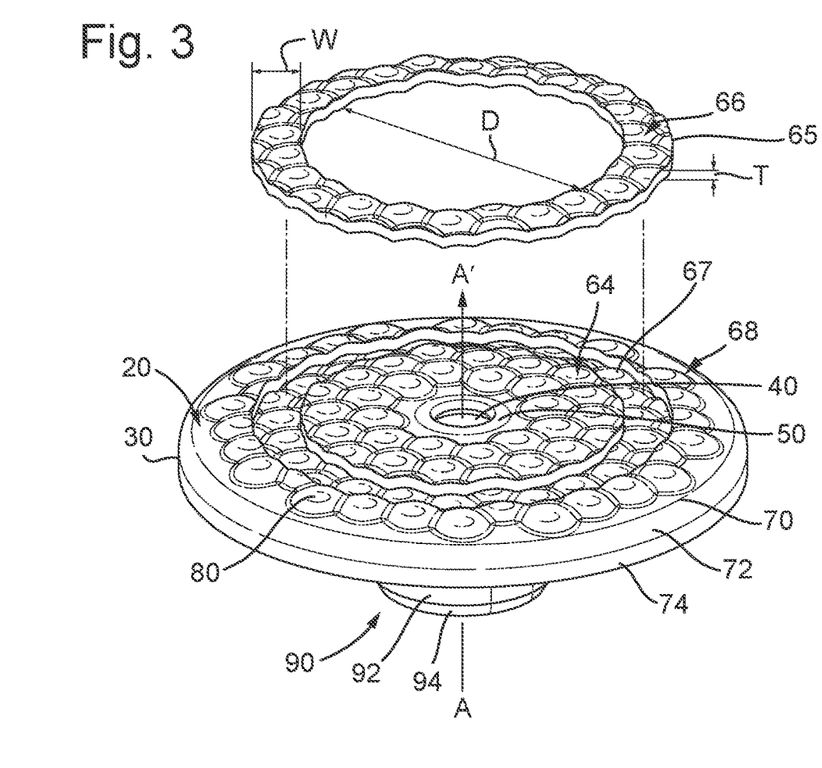
FIG. 3 shows an exploded perspective side view of an applicator surface of the embodiment of FIG. 2.

Preferably, the first and second material are both HDPE materials, but differ in color. The amount of second material injected to form the ring (65) is sufficient to fill the recess (67). Preferably, ring (65) does not project from the applicator surface (20) after cooling. Preferably, ring (65) recesses from the applicator surface (20) by less than about 0.2 mm. In some embodiments, margins of ring (65) flush with margins of recess (67). The ring (65) has an inner diameter D, a ring width W and a thickness T. The outlet opening (40) is positioned in the center of the ring (65). An inner line of demarcation, or inner border, between the first material of the applicator surface body and the second material of the ring (65) constitutes a first dose marking (60'). An outer line of demarcation, or outer border, between the second material of the ring (65) and the first material of the applicator surface body constitutes a second dose marking (62'). The first dose marking (60') has a diameter D, which is the same as the inner ring diameter D, and which is about 20 mm to about 26 mm. The second dose marking (62') has a diameter of about 23 mm to about 29 mm, which is the sum of diameter D and ring width W. The ring (65) divides the applicator surface (20) into an inner dosing compartment (64), a ring dosing compartment (66), and an outer compartment (68). The diameters of the first and second dose marking (60', 62') are adapted such that the inner dosing compartment (64) can accommodate a predefined first dose of a particular topical formulation, and the inner dosing compartment (64) together with the ring dosing compartment (66) can accommodate a predefined second, higher dose of a particular topical formulation. Methods of dosing are described in a separate section below. FIG. 2 and FIG. 3 show such an embodiment, described in more detail below.

Figure 4:
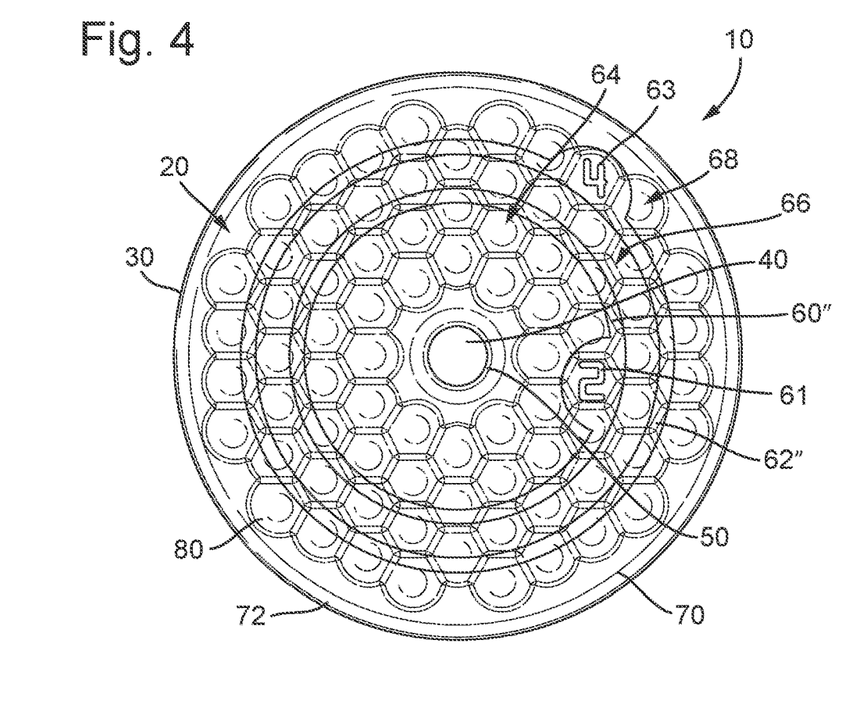
FIG. 4 shows a top view of a third embodiment of an applicator head with dosing aid.
Figure 5:
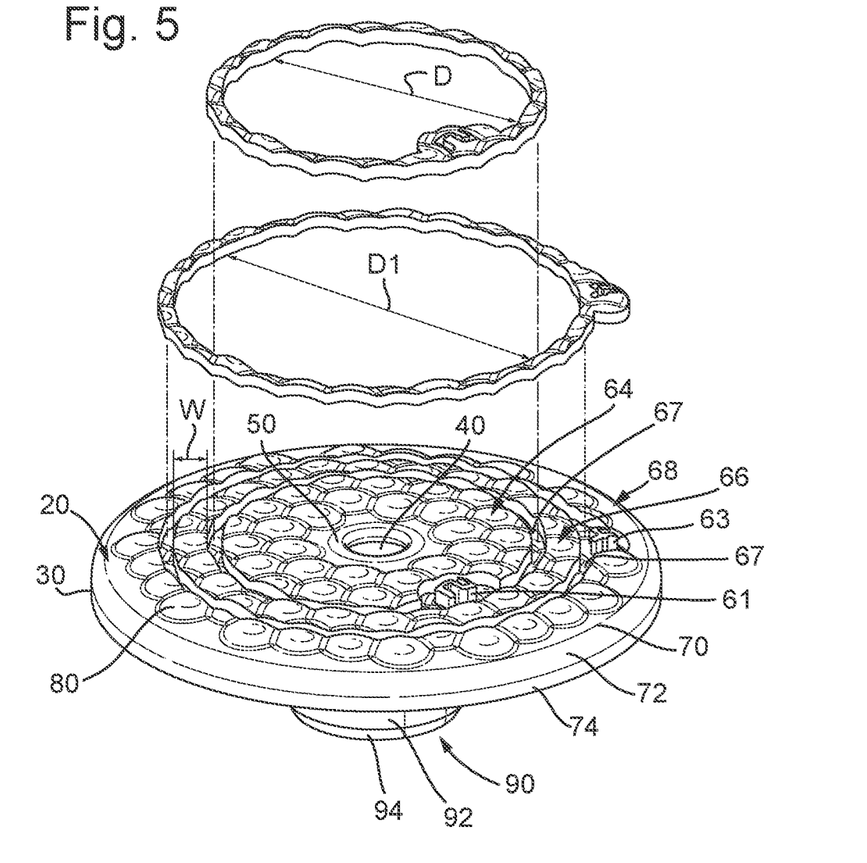
FIG. 5 shows an exploded perspective side view of an applicator surface of the embodiment of FIG. 4.

In another preferred embodiment, the applicator surface (20) comprises two rings. Preferably there are a first and a second ring on the applicator surface. Preferably, the first ring constitutes a first dose marking (60"), and the second ring constitutes a second dose marking (62"). The first dose marking (60") is arranged between the outlet opening (40) and the second dose marking (62"). In this embodiment, the first and second dose marking (60", 62") between them circumscribe a ring dosing compartment (66). First dose marking (60") has an inner diameter D, and an outer diameter. Second dose marking (62") has an inner diameter D1, and an outer diameter. Preferably, D is about to about 19 mm to 21 mm, and D1 is about to about 25 mm to 27 mm. In one embodiment, the thickness of the rings is from about 0.5 mm to about 0.9 mm. Preferably, the rings are about 0.9 mm thick, that is the difference between the outer diameter and the inner diameter (D, D1) is about 0.9 mm. The ring dosing compartment has a ring width W which determined by the difference between the inner diameter D1 of the second dose marking (62") and the outer diameter of the first dose marking (60"). Preferably, the two dose markings (60", 62") are molded into the applicator surface (20). Preferably, the two dose markings (60", 62") have a different color than a rest of the applicator surface (20). This can be achieved by bi-injection molding techniques known in the art. For example, the applicator surface (20) can be molded from HDPE, wherein HDPE of a first color is used for molding of the applicator surface (20), and wherein HDPE of a second color is used for molding of the dose markings (60", 62"). In a first molding step, a body of the applicator surface can be molded from the first material. Two annular recesses (67) can be foreseen on the upper side of the applicator surface (20). The recesses (67) can be about 0.75 mm to about 1.5 mm deep. In a second molding step, the recesses (67) can be filled with the second material to form the two rings or dose markings (60", 62"). The amount of material injected into the two annular recesses (67) is sufficient to fill said recesses (67). The two dose markings (60", 62") thus are rings of the second material molded into the applicator surface (20). After cooling, preferably the dose markings (60", 62") recess from the applicator surface by less than 0.2 mm. Preferably, after cooling the dose markings (60", 62") flush with the applicator surface (20). In other words, the dose markings (60", 62") do not alter a surface profile of the applicator surface (20). The first and second dose marking (60", 62") stand out from the applicator surface (20) as they have a different color. Methods of adjusting inner and outer diameters of the dose markings (60", 62") to predefined doses of topical formulations are described in a separate section below. Methods of dosing with such embodiments are described in a separate section below. FIG. 4 and FIG. 5 show an example of such an embodiment with two rings, and are described in more detail below.

In some embodiments, the dose markings (60, 60', 60", 62', 62") further comprise a dose indicator or dose indicators (61, 63). Dose indicators (61, 63) comprise symbols, such as a figure or a letter, that constitute a clue to a dose. For example, if a dose marking (60, 60', 60") is adapted to measuring a first predefined dose, for example 2 grams, a dose indicator (61) can be a figure "2", present on the applicator surface (20), in association with the dose marking (60, 60', 60"). In embodiments with two or more dose markings (60, 60', 60", 62', 62"), there may be two or more corresponding dose indicators (61, 63). Like the dose markings (60, 60', 60", 62', 62"), the dose indicators (61, 63) can be realized on the applicator surface (20) in numerous ways. For example, the dose indicators (61, 63) can be imprinted, embossed, printed, or they can be realized by surface finish by etching or laser etching. In embodiments with dose marking or dose markings (60, 60', 60", 62', 62") produced by bi-injection molding, it is preferred that the dose indicator or dose indicators (61, 63) are produced in the same bi-injection molding step. In a preferred embodiment, the applicator surface (20) is realized by bi-injection molding, whereby the applicator surface (20) and symbols of the dose indicator(s) (61, 63) are molded from a first material, and the dose marking(s) (60, 60', 60", 62', 62") and an area surrounding the symbols of the dose indicator(s) (61, 63) are molded form a second material. Preferably, in those embodiments, the first and second material have different colors. Thereby, an applicator surface (20) comprising dose marking(s) (60, 60', 60", 62', 62") and dose indicator(s) (61, 63) can be produced within a single bi-injection molding process, wherein the dose indicators (61, 63) are clearly visible.

The applicator head (10) can further comprise a cap and an open-and-closing mechanism. The applicator head (10) can be connected to a container for topical formulations. The applicator head (10) can therefore comprise means (32, 76, 90) for attaching the applicator head to the container.

Adaption of Dimensions of the Dose Markings and Manufacturing Diameter(s) D, D1 of the dose marking(s) (60, 60', 60", 62', 62") and ring width(s) W can be adapted to predefined doses as described below.

To adapt the diameter D of a single dose marking (60) to a single dose of a topical formulation, a prototype of an applicator head (10) with a dose marking (60) of a prototype-diameter is provided. The prototype applicator head is connected to a container, the container containing the topical formulation to be dosed. The container-applicator-head-combination is weighed. Then, the container is held in upright position, i.e., such that the applicator surface (20) is substantially horizontal. Topical formulation is ejected from the outlet opening (40), until it spreads over the applicator surface (20) and reaches the dose marking (60). The ejected topical formulation is then removed from the applicator surface (20). The container-applicator-head-combination is weighed a second time. The difference between the first and second weight corresponds to the ejected amount, or dose, of topical formulation. If the ejected dose is lower than the predefined dose, in a second prototype, diameter D is increased. If the ejected dose is higher than the predefined dose, in a second prototype, diameter D is decreased. The described steps are repeated until an ejected dose corresponds to the predefined dose.

To adapt diameters D of first, second, and further dose markings (60', 60", 62', 62") to first, second and further predefined doses, the above steps are carried out for all dose markings and doses subsequently, starting form the first dose marking (60', 60"), i.e. the dose marking with the smallest diameter D. Ring width(s) W logically follow from the diameters D of the dose markings (60', 60", 62', 62").

The skilled artisan can thereby adapt diameters D to a topical formulation and predefined doses. The applicator heads disclosed herein are especially suitable for topical formulations with a viscosity of about 1 Pa·s to 4 Pa·s, more preferred 1.5 Pa·s to 3.5 Pa·s.

Manufacturing

The applicator head (10) can be molded form plastic material in a single material of any color, preferably white, by an injection molding process. The dose marking(s) (60', 60", 62', 62"), and optionally dose indicators (61, 63), can be realized during the molding process by surface finish difference. For example, dose markings (60', 60", 62', 62"), and optionally dose indicators (61, 63), can be released in a matt surface finish, whilst the applicator surface (20) surrounding the dose marking(s) (60', 60", 62', 62") and dose indicators (61, 63) has a glossy surface finish.

Alternatively, the dose markings (60', 60", 62', 62") can also be embossed onto the applicator surface (20). Preferably, the embossing erects by about 0.25 mm to about 0.75 mm from the applicator surface (20) to create the contrast.

In again another alternative, the dose marking(s) (60', 60", 62', 62"), and optionally dose indicators (61, 63), are realized on the applicator surface (20) in a different color than the applicator surface (20). For example, the dose marking(s) (60', 60", 62', 62"), and optionally dose indicators (61, 63) are realized on the applicator surface (20) by printing, laser engraving or stickering.

For laser etching, the applicator head (10) is loaded onto a laser etching machine. A laser beam follows a preferred path to burn the material in indicated areas on the applicator surface (20) to create the dose marking(s) (60, 60', 60", 62', 62"), and optionally dose indicators (61, 63). This results in the treated areas to be of a different shade of a base color of the applicator surface (20). For example, when the applicator surface (20) is made from a white plastic material, treatment with the laser will yield grey dose marking(s) (60, 60', 60", 62', 62") and optionally dose indicators (61, 63).

A preferred method of manufacturing is manufacturing by bi-injection molding. In a first molding step or shot, a body of the applicator surface (20) can be molded from a first material. In this first molding step or shot, an annular recess (67) is foreseen in the body. Optionally, additional recesses are foreseen for the dose indicators (61, 63). Material is let cool but not ejected from the mold. Subsequently, in a second molding step or shot, recesses are filled with a second material. Preferably, the first and second material are both HDPE materials that differ in color.

Product

There is also provided a packaging for a topical formulation comprising an applicator head as described herein. The packaging comprises a container and an applicator head (10) as described herein, wherein the applicator head (10) is connected to the container or wherein the applicator head (10) is formed in one piece with the container. There is also provided a product, comprising the packaging described herein, and a topical formulation in that packaging. There is also provided a product as described herein, wherein the topical formulation has a viscosity in the range of 1 Pa·s to 4 Pa·s, preferably 1.5 Pa·s to 3.5 Pa·s.

Method

There is also provided a method of dosing of a topical formulation. The method of dosing a first or single predefined dose comprises the following steps:

Holding a package of topical formulation, the package comprising an applicator head (10), the applicator head comprising an applicator surface (20) comprising a dose marking (60, 60', 60") as described herein, in upright position, such that the applicator surface (20) of the applicator head (10) is horizontal;

Urging topical formulation from the package and out of an outlet opening (40) in the applicator surface (20);

Letting the topical formulation spread over the applicator surface (20), until it covers an inner dosing compartment (64);

Stopping urging of topical formulation as soon as the topical formulation covers the inner dosing compartment (64) and before it spreads further beyond the dose marking (60, 60', 60").

The amount of product on the applicator surface (20) corresponds to the first or single predefined dose.

There is also provided a method of dosing a first, second or further predefined dose, the method comprising the following steps:

Holding a package of topical formulation, the package comprising an applicator head (10), the applicator head comprising an applicator surface (20) comprising two or more dose markings (60, 60', 60", 62', 62") as described herein, in upright position, such that the applicator surface (20) of the applicator head is horizontal;

Urging topical formulation from the package and out of an outlet opening (40) in the applicator surface (20);

Letting the topical formulation spread over the applicator surface (20), until it covers an inner dosing compartment (64);

If a first predefined dose is to be measured, stopping urging of topical formulation as soon as the topical formulation covers the inner dosing compartment (64) and before it spreads further beyond a first dose marking (60', 60");

If a second predefined dose is to be measured, continuing urging of topical formulation until the product covers the inner dosing compartment (64) and a ring dosing compartment (66), and stopping urging before the topical formulation spreads further beyond a second dose marking (62', 62");

If a further predefined dose is to be measured, continuing urging of topical formulation until the product covers the inner dosing compartment (64), the ring dosing department (66) and further dosing departments, and stopping urging before the topical formulation spreads further beyond a further dose marking, the further dose marking delimitating a desired dosing compartment.

Preferably, dosing with the dosing aid as described herein achieves a dosing accuracy of +/−10% (wt.).

Exemplary Embodiments

Figure 1:
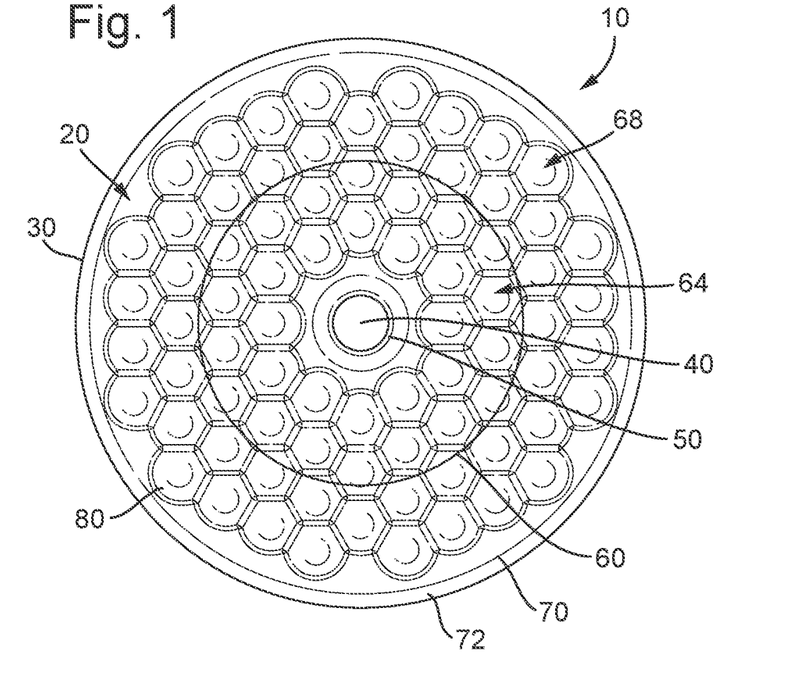
FIG. 1 shows a top view of a first embodiment of an applicator head with dosing aid.

In FIG. 1, FIG. 2 and FIG. 4, three different embodiments of an applicator head (10) with a dosing aid are shown. The three embodiments differ in the elaboration of a dose marking (60) or dose markings (60', 62', 60", 62") on an applicator surface (20).

FIG. 1, FIG. 2 and FIG. 4 show top views of applicator heads (10) for administration of a topical formulation. The applicator head comprises an applicator surface (20). In this top view, the other parts of the applicator head (10) are not visible, as they are eclipsed by the applicator surface (20). The applicator surface (20) is substantially circular. The applicator surface (20) is outwardly limited by an end wall (30). In an area close to the end wall (30), the applicator surface (20) falls away sharply to form a ridge (70). Ridge (70) is connected to an inclined section (72) of the end wall (30). The inclined section (72) of the end wall (30) merges into a vertical section (74) of the end wall (30) (shown e.g., in FIG. 3). Centrally in the substantially circular applicator surface (20) is formed outlet opening (40). The outlet opening (40) is a circular hole in the applicator surface (20). The outlet opening (40) has a diameter of about 5 mm. The outlet opening (40) is connected or connectable to a flow conduit, formed inside the applicator head (10), and connects the flow conduit to the outside. When the applicator head (10) is used with a package for topical formulation, the topical formulation can be urged through the flow conduit and out of the outlet opening (40). The outlet opening (40) is bordered by an outlet rim (50). The outlet rim (50) is a substantially annular protrusion, protruding from the applicator surface (20). The outlet rim (50) has an inner side facing the outlet opening (40). The inner side slopes towards the outlet opening (40). From the sloping inner side, outlet rim (50) erects annularly to a highest level. An outer side of outlet rim (50) is slopes down from the highest level and meets the applicator surface (20) in an obtuse angle. On the highest level, annular outlet rim (50) erects about 1 mm above a level at which it merges with the applicator surface (20).

From the applicator surface (20) protrude surface undulations (80). The surface undulations (80) are bulbous elevations with a blunted, substantially hexagonal outline. The surface undulations (80) are arranged on the applicator surface (20) adjacent to each other, in the form of concentric rings of surface undulations (80), around the outlet opening (40). Some surface undulations (80) have an equilateral hexagonal outline whilst other surface undulations (80) have unequal sided hexagonal outlines. The surface undulations (80) are arranged seamlessly adjoining each other on the circular applicator surface (20). An outermost ring of surface undulations (80), that is a ring furthest remote from the outlet opening (40), is an incomplete ring with a gap every fourth surface undulation (80). A majority of the applicator surface (20) is covered by surface undulations (80). A majority of the applicator surface (20) therefore has a rippled, or wavy, surface profile. An area adjacent to the outlet rim (50) and an area adjacent to the end wall (30) do not have surface undulations (80). These areas therefore have an unrippled, or smooth, profile, and can be referred to as unrippled areas. Sides of surface undulations (80) adjacent to unrippled areas do not have the hexagonal outline, but have their edges facing the unrippled areas rounded.

The applicator surface (20) comprises a dosing aid. The dosing aid comprises a dose marking (60) or dose markings (60', 62', 60", 62").

Referring to FIG. 1, an embodiment of the applicator head (10) is shown comprising one single dose marking (60). The dose marking (60) is a substantially annular line on the applicator surface (20), with the outlet opening (40) in its center. The line is about 0.5 mm thick. The dose marking (60) divides the applicator surface (20) into an inner dosing compartment (64) and an outer compartment (68). In the embodiment of FIG. 1, the applicator surface (20) is made from HDPE and the dose marking (60) is realized on the applicator surface (20) by laser etching of the HDPE. Laser etching is a technique known in the art. After molding, the applicator head (10) is loaded onto a laser etching machine. A laser beam follows a preferred path to burn the material in indicated areas on the applicator surface (20) to create the dose marking (60). This results in the treated area to be of a different shade of a base color of the applicator surface (20).

The dose marking (60) has a diameter D of about 20 mm. The diameter of the dose marking (60) is adapted such that the inner dosing compartment (64) can accommodate a predefined dose of a particular topical formulation. Methods of adapting diameters of dose markings (60, 60', 60", 62', 62") to predefined doses of topical formulations are described above in the detailed description. Methods of dosing with the dose marking are also described above in the detailed description. For dosing of a topical formulation, e.g., a gel, a package comprising the applicator head of FIG. 1 is held in an upright position. By upright it is meant that the applicator surface (20) is horizontal. The gel is urged out of the outlet opening (40) and spreads over the applicator surface (20). The gel forms a blob on the applicator surface (20). When the blob covers the inner dosing compartment (64) and reaches the dose marking (60), urging is stopped. Outer compartment (68) is free from gel. The amount of gel that is now present on the applicator surface (20) corresponds to the predefined dose. In FIG. 1, diameter D is configured to accommodate about 2 grams of the product Voltaren arthritis pain.

FIG. 2 shows another embodiment of the applicator head (10). The embodiment of FIG. 2 has the same features as the embodiment of FIG. 1, except for the elaboration of the dose markings (60', 62'). In the embodiment of FIG. 2, the applicator head (10) is made from HDPE. A ring (65) is molded into the applicator surface (20) from the same HDPE material, but in a different color. The ring (65) has the outlet opening (40) in its center. The ring (65) is molded into the applicator surface (20) by bi-injection molding, which is a technique known in the art. The ring (65) divides the applicator surface (20) into three sections: An inner dosing compartment (64), a ring dosing compartment (66), and an outer compartment (68). A line of demarcation between the ring (65) and the inner dosing compartment (64) constitutes a first dose marking (60'). A line of demarcation between the ring (65) and the outer compartment constitutes a second dose marking (62'). The ring (65) has a ring width W of 6.0 mm, and a diameter D of 20.0 mm (shown in FIG. 3). Consequently, the first dose marking (60') has the same diameter D of 20.0 mm. The second dose marking (62') has a diameter of 26.00 mm, which is the sum of diameter D and ring width W. The diameters of the first and second dose markings (60', 62') are adapted such that the inner dosing compartment (64) can accommodate a predefined first dose of a particular topical formulation, and the inner dosing compartment (64) together with the ring dosing compartment (66) can accommodate a predefined second, higher dose of a particular topical formulation. Methods of adapting diameters of first and second dose markings (60', 62') to predefined first and second doses of topical formulations are described above in the detailed description. Dosing with the dose marking of FIG. 2 is similar to the dosing described in FIG. 1, but the embodiment of FIG. 2 provides for measurement of two different predefined doses. A first dose of topical formulation can be measured as described for FIG. 1 with the inner dosing compartment (64), and a second, higher dose of product can be measured as follows. Urging is not stopped when the product reaches the inner dose marking (60'), but urging is continued until the product spreads further, surmounts the first dose marking (60') and until the product covers the inner dosing compartment (64) and the ring dosing compartment (66), and until it reaches the second dose marking (62'). When the product reaches the second dose marking (62'), urging is stopped. Outer compartment (68) is not covered by product. The amount of product covering the inner dosing compartment (64) and the ring dosing compartment (66) corresponds to a predefined second dose. In FIG. 2, diameter D and ring width W are configured such that the inner dosing compartment (64) accommodates 2 grams of the product Voltaren arthritis pain and the dosing compartment (64) and the ring dosing compartment (66) together accommodate 4 grams of the product Voltaren arthritis pain. The dosing accuracy achieved with this embodiment is +/−10% (wt.).

FIG. 3 shows an exploded perspective side view of an applicator surface (20) of the embodiment of FIG. 2. Especially, ring (65) is shown removed from the applicator surface (20). This is for better understanding of the configuration and manufacturing only, as ring (65) is not necessarily configured to be removed from the applicator surface (20). The applicator surface (20) of the embodiment of FIGS. 2, 3, 6 and 7 is produced by bi-injection molding. In a first molding step, the applicator surface (20) is molded from a first material in a first color. A recess (67) is foreseen in the applicator surface (20) in this first molding step. An arrangement of surface undulations (80) present on the applicator surface (20) is continued on a ground of the recess (67). In a second molding step, this recess (67) is filled with a second material of the ring (66) which has a second color different from the first color. The amount of second material injected to form the ring (65) is sufficient to fill this recess (67). After cooling, ring (65) does not project from the applicator surface (20). Surface undulations (80) present on a surface of the ring (65) fit in seamlessly with an arrangement of surface undulations (80) on a remainder of the applicator surface (20). Ring (65) has a diameter D of 20.0 mm, a width W of 6.0 mm and a thickness T of 0.9 mm. FIG. 3 also shows plug (90) which serves to connect the applicator surface (20) to remaining parts of the applicator head (10). Plug (90) is a tubular protrusion from a bottom side of the applicator surface (20). It is disposed concentric around the outlet opening (40). The plug (90) can accommodate parts of the applicator head (10) that form a flow channel for the topical formulation. Plug (90) protrudes tubularly from the bottom of the applicator surface (20) in a straight plug section (92). Straight plug section (92) is 9 mm long. Plug (90) ends slightly tapered in an inclined plug section (94). The inclined plug section (94) provides easy assembly of the applicator surface (20) with remaining parts of the applicator head (10). The applicator surface (20) can be press-fitted onto remaining parts of the applicator head (10).

FIG. 3 also shows flow direction A-A'. This flow direction A-A' indicates the direction in which a topical formulation, such as a gel or cream, flows, when the applicator surface of FIG. 3 is used with an applicator head (10) for administration. The flow direction A-A' runs through the plug (90) and through the outlet opening (40). FIG. 3 also shows that ridge (70) is connected to inclined section of end wall (72). Inclined section of end wall (72) merges into vertical section of end wall (74). Thereby, a blunted outer edge of applicator surface (20) is provided. This provides for a smooth junction to remaining parts of the applicator head (10). It also renders the haptics of the applicator surface (20) easy to the skin.

FIG. 4 shows yet another embodiment of the applicator head (10). The embodiment of FIG. 4 has the same features as the embodiment of FIG. 1 and FIG. 2, except that the elaboration of the dose markings (60", 62") is yet different. The embodiment of FIG. 4 comprises two rings as the two dose markings (60", 62"), and additionally comprises dose indicators (61, 63).

Both dose markings (60", 62") are realized with rings, arranged concentrically around outlet opening (40). Like ring (65) in the embodiment of FIG. 2, the dose markings (60", 62") are molded into the applicator surface (20). First dose marking (60") is positioned closer to the outlet opening (40) and second dose marking (62") is positioned further outwards from the outlet opening (40). In the embodiment of FIG. 4, the applicator head (10) is made from HDPE and the first and second dose markings (60", 62") are molded from the same material, but in a different color. The applicator surface (10) comprising the two dose markings (60", 62") is manufactured by bi-injection molding, a technique known in the art. The first and second dose markings (60", 62") stand out from the applicator surface (20) as they are colored differently. The dose markings (60", 62") additionally comprise dose indicators (61, 63). The dose indicators (61, 63) are figures, formed within semi-circular bulges, the bulges being formed within dose marking rings (60", 62"). In FIG. 3, dose indicators (61, 63) indicate the predefined doses of 2 grams (61) and 4 grams (63) with the figures "2" and "4". The figures are from the same material and color as the applicator surface (20). Consequently, the figures stand out from the differently colored bulges of the dose markings (60", 62"), and are easily legible. The figure in the first dose indicator (61) of the first dose marking (60") stands for a first predefined dose which can be measured with this first dose marking (60"). The figure in the second dose indicator (63) in the second dose marking (62") stands for a second predefined dose which can be measured with the second dose marking (62").

The two dose markings (60", 62") divide the applicator surface (20) into three sections: An inner dosing compartment (64), a ring dosing compartment (66), and an outer compartment (68). The ring dosing compartment (66) in this embodiment is restricted by an outer margin of the first dose marking (60") and an inner margin of the second dose marking (62"). The ring dosing compartment (66) has a ring width W. The first dose marking (60") has an inner diameter D of 19.55 mm and an outer diameter of 20.45 mm (shown in FIG. 5). The second dose marking (62") has an inner diameter D1 of 25.55 mm and an outer diameter of 26.45 mm (shown in FIG. 5). The diameters of the first and second dose marking (60", 62") are adapted such that the inner dosing compartment (64) can accommodate a predefined first dose of a particular topical formulation, and the inner dosing compartment (64), together with the ring dosing compartment (66) can accommodate a predefined second, higher dose of a particular topical formulation. Methods of adapting diameters of first and second dose markings (60", 62") to predefined first and second doses of topical formulations are described in the detailed description.

Dosing of a with the embodiment of FIG. 4 works as follows. A packaging comprising the applicator head of FIG. 4 is held in upright position such that the applicator surface (20) is horizontal. Topical formulation is urged from the packaging and out of the outlet opening (40). The formulation spreads over the applicator surface (20) in a blob. If a first dose of formulation is desired, urging is continued until the product reaches the first dose marking (60"). If the urging is stopped when the formulation is on an inner edge of first dose marking (60"), on the first dose marking (60"), or on an outer edge of first dose marking (60"), the dose measured will be within the range of 2 grams+/−10% (wt) of Voltaren arthritis pain. The formulation covers the inner dosing compartment (64) and the first dose marking (62"). The ring dosing compartment (66), the second dose marking (62"), and the outer compartment (68) are not covered by product. The amount of product now present on the applicator surface (20) is the predefined first dose, namely 2 grams of Voltaren arthritis pain. The dose indicator (61) reminds a user of an amount of product that is the first dose, in this embodiment, 2 grams. If a second, higher dose of product is desired, urging is continued until the product reaches and covers the second dose marking (62"). The product covers the inner dosing compartment (64), the first dose marking (60"), the ring dosing compartment (66), and the second dose marking (62"). The outer compartment (68) is not covered by product. The amount of Voltaren arthritis pain now present on the applicator surface (20) is the predefined second dose, namely 4.0 grams of XX. The dose indicator (63) reminds a user of an amount of product that is the second dose, in this embodiment, 4 grams.

FIG. 5 shows an exploded perspective side view of an applicator surface of the embodiment of FIG. 4. As in FIG. 3, the dose markings (60", 62") is shown removed from the applicator surface (20). This is for better understanding of the configuration and manufacturing only, as the dose markings (60", 62") are not necessarily configured to be removed from the applicator surface (20). The applicator surface (20) of FIG. 4 and FIG. 5 is produced by bi-injection molding. In a first molding step, the applicator surface (20) is molded from a first material in a first color. Two recesses (67) are foreseen in the applicator surface (20) in this first molding step. Significantly, the recesses (67) foresee also a recessed space for the bulges surrounding the dose indicators (61, 63). Within these recessed spaces there are formed, still from the first material in the first color, and during the first molding step, figures of the dose indicators (61, 63). An arrangement of surface undulations (80) present on the applicator surface (20) is continued on a ground of the recess (67). In a second molding step, the recesses are filled with a second material of the first and second dose markings (60", 62"), which has a second color different from the first color. The amount of second material injected to form the two dose markings (60", 62") is sufficient to fill the recesses (67). After cooling, dose markings (60", 62") do not project from the applicator surface (20). Margins of dose markings (60", 62") flush with margins of recesses (67). Surface undulations (80) present on surface of the dose markings (60", 62") fit in seamlessly with an arrangement of surface undulations (80) on a remainder of the applicator surface (20). The applicator surface (20) has a smooth surface, regularly rippled due to the surface undulations (80). The dose markings (60", 62") have the same thickness as thickness T of the ring (65) in FIG. 3. Plug (90) is configured as in the embodiment of FIG. 3.

Figure 6:
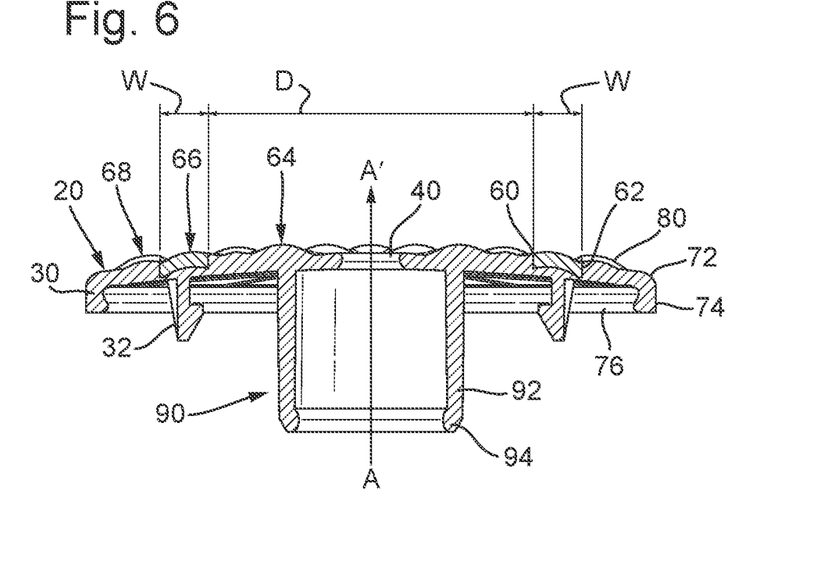
FIG. 6 shows a central vertical cut view of an applicator surface of the embodiment of FIG. 2.

FIG. 6 shows a vertical central cut view of an applicator surface of the embodiment of FIG. 2. Applicator surface (20) has a bumpy or rippled surface due to surface undulations (80). Furthermore, applicator surface (20) has a slight curvature with a highest point centrally, close to the outlet opening (40) and a lowest point outwardly, close to the end wall (30). FIG. 6 shows how flow direction A-A' runs through an inside of plug (90) and out of outlet opening (40). Plug (90) protrudes from a bottom side of the applicator surface (20) in an approximately right angle. A surface of plug (90) facing the flow direction A-A' has a smooth surface. Plug (90) is configured to be slidable vis-à-vis remaining parts of the applicator head (10).

Fixing elements (32) are foreseen on a bottom of the applicator surface (20). The fixing elements (32) are hooks of about 3.75 mm length. There are two fixing elements in the embodiment of FIG. 6 (only 2 shown). The fixing elements are positioned approximately under the recess (67) and ring (66). With fixing elements (32), the applicator head (20) can be affixed to remaining parts of the applicator head (10) with a snap fit mechanism, such that a user cannot remove it. Additionally, annular fixing element (76) is formed on an end of vertical section of end wall (74) that faces the plug (90). Annular fixing element (76) also affixes to remaining parts of the applicator head by way of snap fit and ensures that the applicator surface (20) stays connected to remaining parts of the applicator head (10) even when an open and closing mechanism foreseen in the applicator head (10) is opened.

Figure 7:
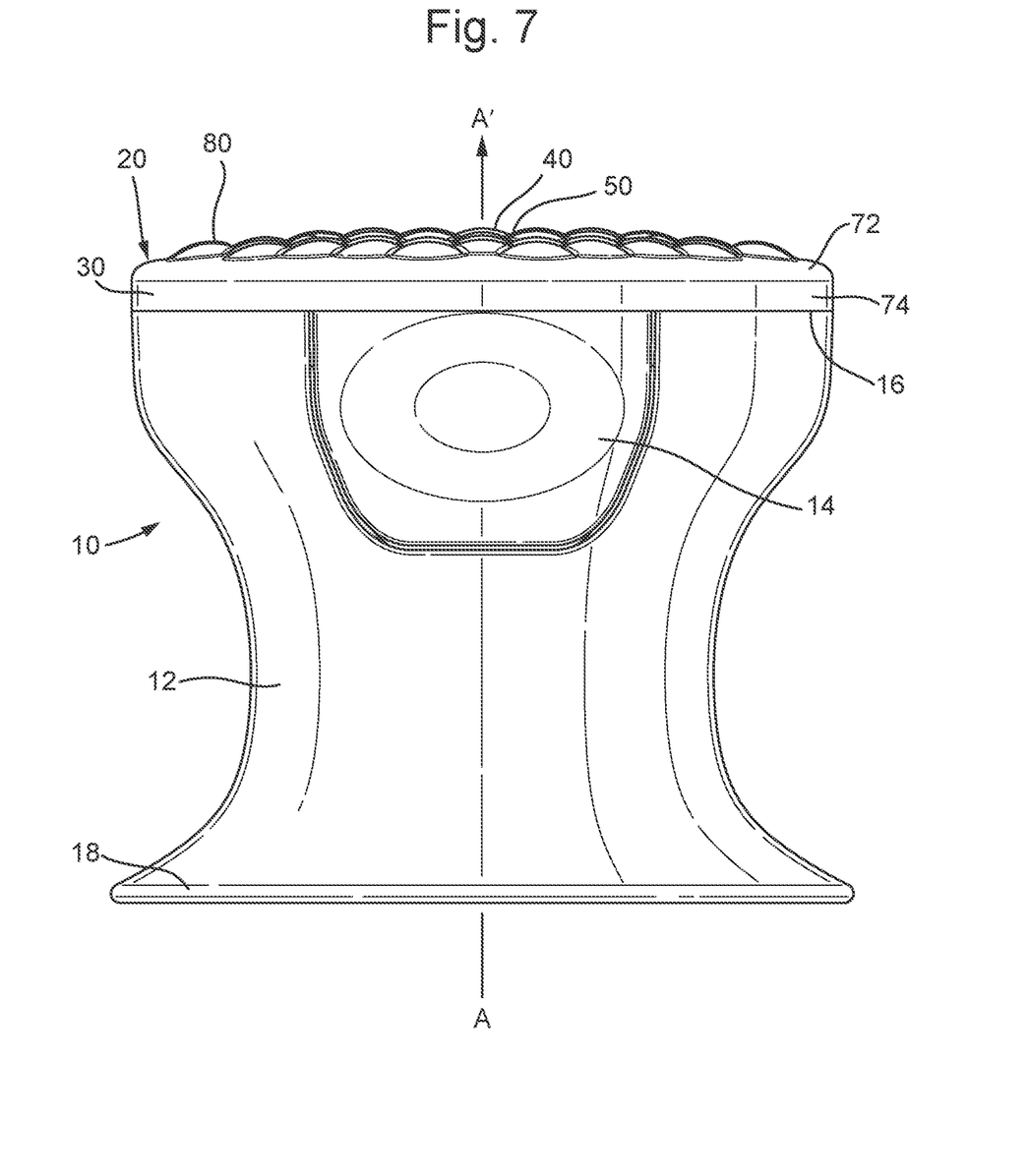
FIG. 7 shows a side view of the embodiment of FIG. 2.
Figure 8:
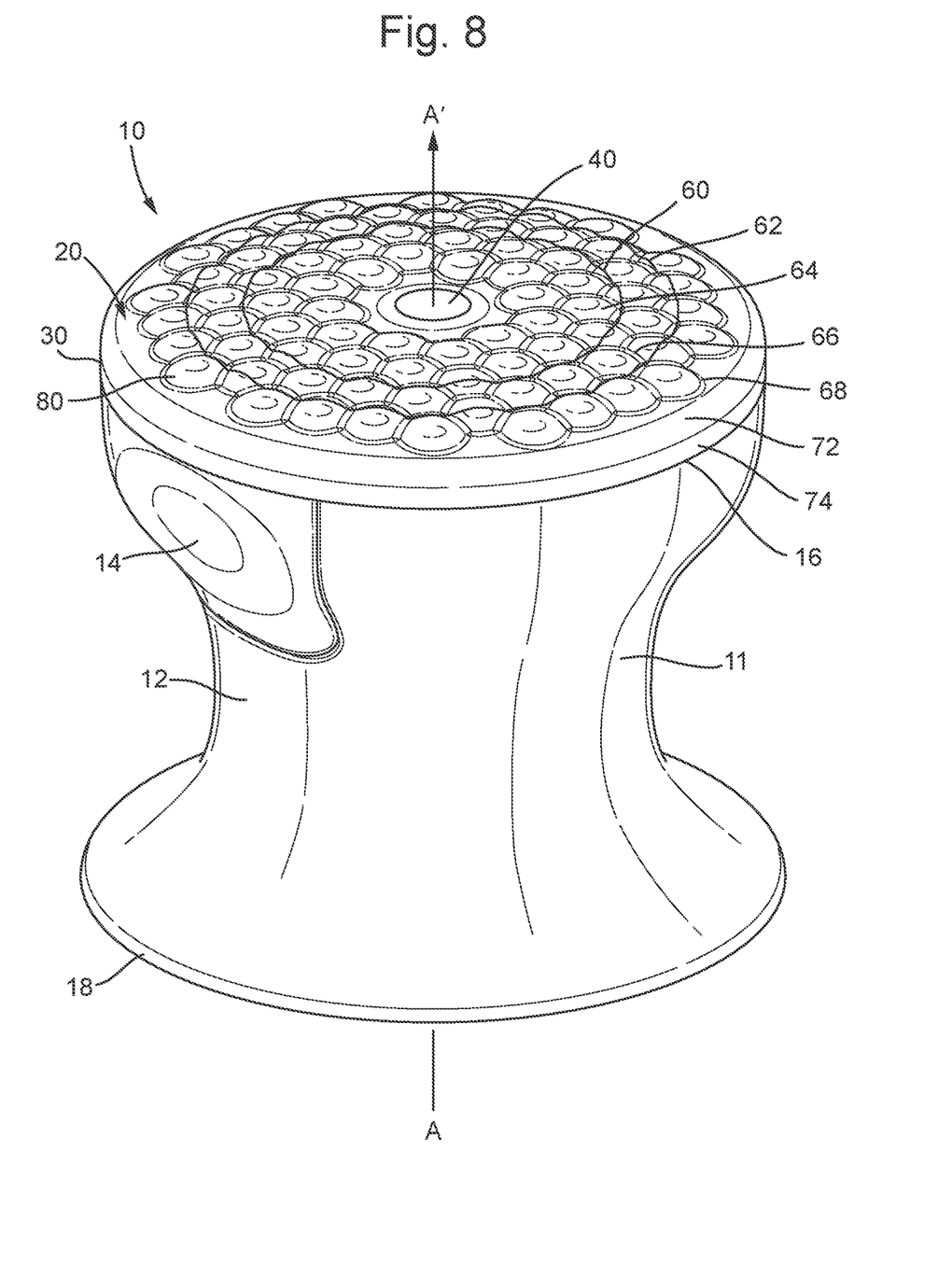
FIG. 8 shows a perspective external view of the embodiment of FIG. 2.

FIG. 7 shows a side view of the embodiment of FIG. 2. Especially, in FIG. 7, the applicator surface (20) of FIG. 2 is affixed to remaining parts of the applicator head (10). From the applicator surface (20), applicator head (10) tapers towards a neck part (12) before it widens up again towards a tube transition section (18). Tube transition section (18) has a form and dimensions that match a neck part of a tube or container to be used with the applicator head (10). In an upper half of the applicator head (10), grip portions (14) are foreseen. There are two grip portions (14) on opposite sides of applicator head (10). In FIGS. 7 and 8, only one grip portion (14) is visible. Grip portions (14) serve to operate an open and closing mechanism foreseen in the applicator head (10). FIG. 7 shows the applicator head (10) in closed position. In closed position, the vertical section (74) of end wall (30) meets a body (11) of applicator head (10) in a line of contact (16). To open applicator head (10), lifting force in the flow direction A-A' is applied on the applicator surface (20) through grip portions (14). Applicator surface (20) then lifts about 2.5 mm from body (11) in a slide motion, until it reaches a maximum open position. To close the applicator head, pulling force is applied on the applicator surface (20) via grip portions (14) in a closing direction A'-A. Applicator surface (20) then slides in this closing direction A'-A until it meets body (11) in a closed position.

FIG. 8 shows a perspective external view of the embodiment of FIG. 2. It shows that grip portions (14) are designed ergonomically with recesses that accommodate fingers of a user. The grip portions (14) can thus be easily grabbed. The open and closing mechanism can thus be operated with two fingers, typically a thumb on one grip portion (14) and an index finger of the same hand on the second grip portion (14). FIG. 8 also shows the applicator head (10) in a closed position. Therefore, there is no distance between the applicator surface (20) and the body (11).

Elements, apparatus, and methods described herein, however, are not limited to the specific embodiments presented in the detailed description, examples, and figures. It should be recognized that the exemplary embodiments herein are merely illustrative of the principles of the present invention. Numerous modifications and adaptations will be readily apparent to those of skill in the art without departing from the spirit and scope of the invention.

In addition, all ranges disclosed herein are to be understood to encompass any and all subranges subsumed therein. For example, a stated range of "1.0 to 10.0" should be considered to include any and all subranges beginning with a minimum value of 1.0 or more and ending with a maximum value of 10.0 or less, e.g., 1.0 to 5.3, or 4.7 to 10.0, or 3.6 to 7.9.

All ranges disclosed herein are also to be considered to include the end points of the range, unless expressly stated otherwise. For example, a range of "between 5 and 10" or "5 to 10" or "5-10" should generally be considered to include the end points 5 and 10.

It is further to be understood that the feature or features of one embodiment may generally be applied to other embodiments, even though not specifically described or illustrated in such other embodiments, unless expressly prohibited by this disclosure or the nature of the relevant embodiments. Likewise, compositions and methods described herein can include any combination of features and/or steps described herein not inconsistent with the objectives of the present disclosure. Numerous modifications and/or adaptations of the compositions and methods described herein will be readily apparent to those skilled in the art without departing from the present subject matter.

The invention claimed is:

1. An applicator head for administration of a topical formulation, comprising a dosing aid for application of a predefined dose of the topical formulation, wherein the applicator head comprises an applicator surface adapted to apply the topical formulation to a user's skin, wherein the applicator surface comprises an outlet opening, and wherein the dosing aid comprises a dose marking on the applicator surface, wherein the dose marking is only a visual dose marking, wherein the dose marking has a circular outline and a diameter D, and wherein the outlet opening is disposed in the center of the circular outline, and wherein the dose marking circumscribes an inner dosing compartment that serves to measure the predefined dose of the topical formulation.

2. An applicator head according to claim 1, wherein the diameter D is selected such that, when the topical formulation is ejected from the outlet opening, the amount of topical formulation that spreads from the outlet opening and over the inner dosing compartment until it reaches the dose marking, corresponds to the predefined dose.

3. An applicator head according to claim 1, wherein the dose marking is realized on the applicator surface by surface treatment of the applicator surface, application of color markings on the applicator surface, by producing the applicator surface from several materials, wherein a border between two distinct materials serves as the dose marking, or by moulding-in of the dose marking into the applicator surface.

4. An applicator head according to claim 3, wherein the dose marking has a color that is different from the color of a rest of the applicator surface.

5. An applicator head according to claim 1, wherein the dose marking flushes with the applicator surface.

6. An applicator head according to claim 1, wherein the dosing aid is adapted for dosing of two predefined doses of topical formulation.

7. An applicator head according to claim 1, wherein there is more than one dose marking on the applicator surface, and wherein the dose markings are arranged on the applicator surface concentrically around the outlet opening.

8. An applicator head according to claim 7, wherein there are a first and a second dose marking on the applicator surface, wherein the first dose marking is arranged between the outlet opening and the second dose marking, and wherein the first and second dose marking between them circumscribe a ring dosing compartment, and wherein the ring dosing compartment has a ring width W that is the distance between the first and the second dose marking.

9. An applicator head according to claim 8, wherein the ring width W is selected such that when the topical formulation is ejected from the outlet opening, the amount of topical formulation that spreads from the outlet opening and over the inner dosing compartment and further over the ring dosing compartment, until it reaches the second dose marking, corresponds to a second predefined dose.

10. An applicator head according to claim 8, wherein the applicator surface is manufactured by bi-injection moulding.

11. An applicator head according to claim 8, wherein the diameter D of the first dose marking is about 19 mm to about 21 mm.

12. An applicator head according to claim 8, wherein the diameter D of the second dose marking is about 25 mm to about 27 mm and the ring width W is from about 0.8 mm to about 3 mm.

13. An applicator head for administration of a topical formulation, comprising a dosing aid for application of a predefined dose of the topical formulation, wherein the applicator head comprises an applicator surface adapted to apply the topical formulation to a user's skin, wherein the applicator surface comprises multiple outlet openings, and wherein the dosing aid comprises a dose marking on the applicator surface, wherein the dose marking is only a visual dose marking, wherein the dose marking has a circular outline and a diameter D, and wherein the outlet openings are disposed on the applicator surface point symmetrical to a center of the circular outline, and wherein the dose marking circumscribes an inner dosing compartment that serves to measure the predefined dose of the topical formulation.

14. A packaging for a topical formulation comprising an applicator head according to claim 1.

15. A product comprising a packaging according to claim 13 containing a topical formulation.

16. A product according to claim 14, wherein the topical formulation has a viscosity in the range of 1 Pa·s to 4 Pa·s.

17. A method of dosing the topical formulation according to claim 14 comprising the steps of:
  urging the topical formulation from the packaging and out of the outlet opening on the applicator surface, letting the topical formulation spread over the applicator surface until it covers the inner dosing compartment, and stopping urging of the topical formulation as soon as the topical formulation covers the inner dosing compartment.

* * * * *